United States Patent
Dong et al.

(10) Patent No.: US 10,499,149 B2
(45) Date of Patent: Dec. 3, 2019

(54) MICROPHONE, VOCAL TRAINING APPARATUS COMPRISING MICROPHONE AND VOCAL ANALYZER, VOCAL TRAINING METHOD, AND NON-TRANSITORY TANGIBLE COMPUTER-READABLE STORAGE MEDIUM

(71) Applicant: BOE TECHNOLOGY GROUP CO., LTD., Beijing (CN)

(72) Inventors: Wenchu Dong, Beijing (CN); Zhenglong Li, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 15/766,077

(22) PCT Filed: Nov. 15, 2017

(86) PCT No.: PCT/CN2017/111038
§ 371 (c)(1),
(2) Date: Apr. 5, 2018

(87) PCT Pub. No.: WO2018/201688
PCT Pub. Date: Nov. 8, 2018

(65) Prior Publication Data
US 2019/0124441 A1  Apr. 25, 2019

(30) Foreign Application Priority Data

May 5, 2017 (CN) .......................... 2017 1 0311882

(51) Int. Cl.
*H04R 3/00* (2006.01)
*G10L 25/30* (2013.01)
(Continued)

(52) U.S. Cl.
CPC .............. *H04R 3/005* (2013.01); *G10L 25/30* (2013.01); *G10L 25/60* (2013.01); *G10L 25/66* (2013.01); *H04R 1/08* (2013.01); *H04R 3/00* (2013.01)

(58) Field of Classification Search
CPC ......... G10L 25/30; G10L 25/60; G10L 25/66; H04R 1/08; H04R 3/005
See application file for complete search history.

(56) References Cited

FOREIGN PATENT DOCUMENTS

| CN | 101739870 A | 6/2010 |
|---|---|---|
| CN | 102342858 A | 2/2012 |

(Continued)

OTHER PUBLICATIONS

Fang, English Translation of CN105962895 "User State Reminding Method and System", Sep. 28, 2016.*

(Continued)

*Primary Examiner* — Regina N Holder
(74) *Attorney, Agent, or Firm* — Intellectual Valley Law, P.C.

(57) ABSTRACT

The present application discloses a microphone. The microphone includes a voice sensor configured to collect an audio signal; a converter connected to the voice sensor and configured to convert the audio signal into a digital audio signal; a signal transceiver connected to the converter and configured to transmit the digital audio signal and receive a voice status determination signal generated based on the digital audio signal; and an indicator configured to generate one or more indication signals based on the voice status determination signal. The voice status determination signal includes one or a combination of an acoustic quality determination signal and a health status determination signal. The one or (Continued)

more indication signals includes one or a combination of an acoustic quality indication signal and a health status indication signal.

18 Claims, 4 Drawing Sheets

(51) Int. Cl.
    *G10L 25/60*     (2013.01)
    *H04R 1/08*     (2006.01)
    *G10L 25/66*     (2013.01)

(56) References Cited

FOREIGN PATENT DOCUMENTS

| CN | 202475713 U | 10/2012 |
|---|---|---|
| CN | 203289603 U | 11/2013 |
| CN | 204069242 U | 12/2014 |
| CN | 104732977 A | 6/2015 |
| CN | 105596016 A | 5/2016 |
| CN | 105962895 A | 9/2016 |
| CN | 106073706 A | 11/2016 |
| CN | 106250400 A | 12/2016 |
| CN | 106878840 A | 6/2017 |
| CN | 107331378 A | 11/2017 |
| CN | 107371075 A | 11/2017 |
| CN | 206726760 U | 12/2017 |
| WO | 2008054162 A1 | 5/2008 |

OTHER PUBLICATIONS

Liu et al., English Translation of CN202475713"Integrated microphone based on pure voice operation", Oct. 3, 2012.*
Wang, English Translation of CN203289603 "Wireless Microphone", Nov. 13, 2013.*
Chen, English Translation of CN204069242, "Multifunctional microphone", Dec. 31, 2014.*
Lin et al., English Translation of CN104732977, "Online spoken language pronunciation quality evalutation method and system", Jun. 24, 2015.*
International Search Report & Written Opinion dated Feb. 23, 2018, regarding PCT/CN2017/111038.
First Office Action in the Chinese Patent Application No. 201710311882.7, dated Apr. 11, 2019; English translation attached.

* cited by examiner

MICROPHONE, VOCAL TRAINING APPARATUS COMPRISING MICROPHONE AND VOCAL ANALYZER, VOCAL TRAINING METHOD, AND NON-TRANSITORY TANGIBLE COMPUTER-READABLE STORAGE MEDIUM

CROSS-REFERENCE TO RELATED APPLICATION

This application is a national stage application under 35 U.S.C. § 371 of International Application No. PCT/CN2017/11038, filed Nov. 15, 2017, which claims priority to Chinese Patent Application No. 201710311882.7, filed May 5, 2017, the contents of which are incorporated by reference in the entirety.

TECHNICAL FIELD

The present invention relates to smart apparatuses, more particularly, to a microphone, a vocal training apparatus having a microphone and a vocal analyzer, a vocal training method, and a non-transitory tangible computer-readable storage medium.

BACKGROUND

A microphone is a transducer that converts sound into an electrical signal. Several different types of microphone are in use, which employ different methods to convert the air pressure variations of a sound wave to an electrical signal. The most common are the dynamic microphone, which uses a coil of wire suspended in a magnetic field. A condenser microphone uses the vibrating diaphragm as a capacitor plate. A piezoelectric microphone uses a crystal of piezoelectric material. Examples of microphones also include a digital microphone.

SUMMARY

In one aspect, the present invention provides a microphone comprising a voice sensor configured to collect an audio signal; a converter connected to the voice sensor and configured to convert the audio signal into a digital audio signal, a signal transceiver connected to the converter and configured to transmit the digital audio signal and receive a voice status determination signal generated based on the digital audio signal; and an indicator configured to generate one or more indication signals based on the voice status determination signal; wherein the voice status determination signal comprises one or a combination of an acoustic quality determination signal and a health status determination signal; and the one or more indication signals comprises one or a combination of an acoustic quality indication signal and a health status indication signal.

Optionally, the microphone further comprises a biometric sensor configured to detect one or more biometric signals; wherein the health status determination signal is generated based on a combination of the digital audio signal and the one or more biometric signals; the signal transceiver is connected to the biometric sensor, and configured to transmit the one or more biometric signals detected by the biometric sensor and receive the health status determination signal; and the one or more indication signals comprises the health status indication signal.

Optionally, the one or more biometric signals comprises one or a combination of a body temperature signal, a pulse wave signal, a blood oxygen level signal, a heart rate signal, and a blood pressure signal.

Optionally, the indicator comprises one or a combination of an indicator light for generating an optical signal; and a display panel for generating an image signal.

Optionally, the microphone comprises a shell; the shell comprises a head part and a handle part; the voice sensor is enclosed by the head part of the shell; the biometric sensor is on an outer wall of the handle part of the shell; the indicator light is enclosed by the head part of the shell which is configured to allow light pass through; and the display panel is on the outer wall of the handle part.

Optionally, the microphone further comprises an authenticator configured to collect an identification information of a user; the signal transceiver is connected to the authenticator and configured to transmit the identification information.

Optionally, the authenticator is on the outer wall of the handle part; and the identification information of the user includes a fingerprint information of the user.

In another aspect, the present invention provides a vocal training apparatus comprising the microphone described herein.

Optionally, the vocal training apparatus further comprises a vocal analyzer, wherein the vocal analyzer comprises a signal receiver configured to receive the digital audio signal transmitted by the signal transceiver; a voice status determinator connected to the signal receiver and configured to generate the voice status determination signal based on the digital audio signal; and a signal transmitter connected to the voice status determinator and configured to transmit the voice status determination signal to the signal transceiver.

Optionally, the voice status determinator comprises an acoustic quality determinator configured to determine an acoustic quality of the digital audio signal by calculating a degree of similarity between a note in the digital audio signal and a target note.

Optionally, the degree of similarity between a note in the digital audio signal and a target note is calculated using a first convolutional neural network model.

Optionally, the microphone further comprises a biometric sensor configured to detect one or more biometric signals; the signal transceiver is connected to the biometric sensor, and configured to transmit the one or more biometric signals detected by the biometric sensor to the signal receiver and receive the health status determination signal from the signal transmitter, the voice status determinator further comprises a health status determinator configured to classify a health status of a user based on the digital audio signal and the one or more biometric signals, and generate the health status determination signal based on a combination of the digital audio signal and the one or more biometric signals.

Optionally, the health status of the user is classified using a second convolutional neural network model.

Optionally, the voice status determinator further comprises a pre-processor configured to pre-process the digital audio signal and the one or more biometric signals.

Optionally, the degree of similarity between a note in the digital audio signal and a target note is calculated based a similarity calculation model trained using a plurality of first reference audio signals and a plurality of reference degrees of similarity associate therewith; and the health status of the user is classified based on a classification model trained using a plurality of second reference audio signals, a plurality of reference biometric signals, and a plurality of reference health status classifications associated therewith.

Optionally, the vocal training apparatus further comprises an updater connected to the voice status determinator and configured to update the similarity calculation model using a data comprising the digital audio signal and the degree of similarity calculated based on the digital audio signal; and update the classification model using a data comprising the digital audio signal, the one or more biometric signals, and the health status classified based on the digital audio signal and the one or more biometric signals.

Optionally, the microphone further comprises an authenticator configured to collect an identification information of a user; the signal transceiver is connected to the authenticator and configured to transmit the identification information to the signal receiver, the vocal analyzer further comprises a data base comprising a plurality of biometric information of a plurality of users, a plurality of acoustic quality information of the plurality of users, and a plurality of health status information of the plurality of users.

Optionally, the vocal analyzer further comprises a feedback generator connected to the voice status determinator and configured to generate a first feedback signal based on the acoustic quality of the digital audio signal and a second feedback signal based on the health status of the user, the signal transmitter is connected to the feedback generator and configured to transmit the first feedback signal and the second feedback signal to the signal transceiver; and the indicator comprises a display panel configured to display a plurality of vocal training instructions based on the first feedback signal and a plurality of health guidance instructions based on the second feedback signal.

Optionally, the vocal training apparatus is a smart microphone having the microphone and the vocal analyzer integrated into the microphone.

In another aspect, the present invention provides a vocal training method, comprising generating an acoustic quality determination signal based on a digital audio signal; and generating one or more indication signals based on the acoustic quality determination signal, the one or more indication signals comprising an acoustic quality indication signal.

In another aspect, the present invention provides a non-transitory tangible computer-readable storage medium storing computer-readable instructions, the computer-readable instructions being executable by a processor to cause the processor to perform generating an acoustic quality determination signal based on a digital audio signal; and generate one or more indication signals based on the acoustic quality determination signal, the one or more indication signals comprising an acoustic quality indication signal.

BRIEF DESCRIPTION OF THE FIGURES

The following drawings are merely examples for illustrative purposes according to various disclosed embodiments and are not intended to limit the scope of the present invention.

DETAILED DESCRIPTION

The disclosure will now be described more specifically with reference to the following embodiments. It is to be noted that the following descriptions of some embodiments are presented herein for purpose of illustration and description only. It is not intended to be exhaustive or to be limited to the precise form disclosed.

The present disclosure provides, inter alia, a microphone, a vocal training apparatus comprising a microphone and a vocal analyzer, a vocal training method, and a non-transitory tangible computer-readable storage medium that substantially obviate one or more of the problems due to limitations and disadvantages of the related art. In one aspect, the present disclosure provides a microphone. In some embodiments, the microphone includes a voice sensor configured to collect an audio signal; a converter connected to the voice sensor and configured to convert the audio signal into a digital audio signal; a signal transceiver connected to the converter and configured to transmit the digital audio signal and receive a voice status determination signal generated based on the digital audio signal; and an indicator configured to generate one or more indication signals based on the voice status determination signal. Optionally, the voice status determination signal includes one or a combination of an acoustic quality determination signal and a health status determination signal. Optionally, the one or more indication signals includes one or a combination of an acoustic quality indication signal and a health status indication signal.

Figure 1:
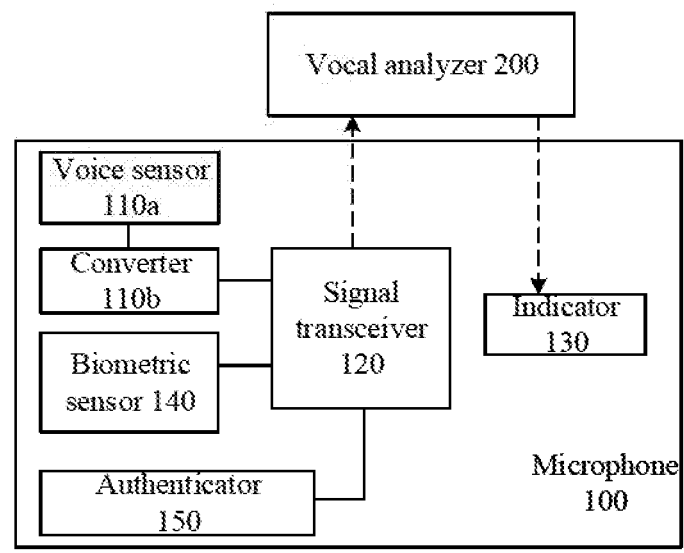
FIG. 1 is a schematic diagram illustrating the structure of a microphone in some embodiments according to the present disclosure.

FIG. 1 is a schematic diagram illustrating the structure of a microphone in some embodiments according to the present disclosure. Referring to FIG. 1, the microphone in some embodiments includes a voice sensor 110a, a converter 110b, a signal transceiver 120, and an indicator 130. The voice sensor 110a is configured to collect an audio signal. The converter 110b is connected to the voice sensor 110a and is configured to convert the audio signal into a digital audio signal. The signal transceiver 120 is connected to the converter 110b and configured to transmit the digital audio signal (e.g., to a vocal analyzer 200) and receive a voice status determination signal (e.g., from the vocal analyzer 200) generated based on the digital audio signal. Optionally, the voice status determination signal includes an acoustic quality determination signal. Optionally, the converter 110b is connected to the signal transceiver 120 by wire. Optionally, the converter 110b is connected to the signal transceiver 120 wirelessly. Optionally, the voice status determination signal is generated by the vocal analyzer 200.

In some embodiments, the microphone further includes a biometric sensor 140 configured to detect one or more biometric signals of a user. Optionally, the voice status determination signal includes a health status determination signal. Optionally, the health status determination signal is generated based on the one or more biometric signals. Optionally, the health status determination signal is generated based on a combination of the digital audio signal and the one or more biometric signals. Optionally, the signal transceiver 120 is connected to the biometric sensor 140, and is configured to transmit the one or more biometric signals detected by the biometric sensor 140 (e.g., to the vocal analyzer 200) and receive the health status determination signal (e.g., from the vocal analyzer 200). Optionally, the biometric sensor 140 is connected to the signal transceiver 120 by wire. Optionally, the biometric sensor 140 is connected to the signal transceiver 120 wirelessly. Optionally, the health status determination signal is generated by the vocal analyzer 200. Optionally, the one or more indication signals includes a health status indication signal.

In some embodiments, the microphone is used for vocal training by a user, e.g., a singer or a news anchor. Optionally, the acoustic quality in the context of the present disclosure refers to a degree of similarity between a sound produced by the user in the vocal training and a target sound, e.g., the degree of similarity in terms of a tune, a pitch, a volume of the sound. Optionally, the acoustic quality refers to a degree of similarity between a note in a sound produced by the user in the vocal training and a target note. Optionally, the health status in the context of the present disclosure refers to health status of a vocal organ (e.g., a vocal cord, a throat) of the user. Examples of health status of the vocal organ include fatigue (e.g., fatigue of the vocal cord), overuse or misuse (e.g., overuse or misuse of the vocal cord), and pathological change (e.g., pathological change of the throat). The one or more indication signals may be an optical signal, an audio signal, a vibration signal, a text signal, a graphic signal, or a combination thereof.

In the present microphone, the microphone 100 transmits the digital audio signal to the vocal analyzer 200. The vocal analyzer 200 is configured to determine an acoustic quality of the digital audio signal, configured to generate an acoustic quality determination signal, and configured to transmit the acoustic quality determination signal to the microphone 100 (e.g., the signal transceiver 120 of the microphone 100). Optionally, the vocal analyzer 200 is further configured to classify a health status of a user (e.g., based on the digital audio signal or based on a combination of the digital audio signal and the one or more biometric signals), configured to generate a health status determination signal, and configured to transmit the health status determination signal to the microphone 100 (e.g., the signal transceiver 120 of the microphone 100). Upon receiving the acoustic quality determination signal from the vocal analyzer 200, the indicator 130 is configured to generate an acoustic quality indication signal. Upon receiving the health status determination signal from the vocal analyzer 200, the indicator 130 is configured to generate a health status indication signal. The user can quickly assess the acoustic quality and health status upon receiving the acoustic quality indication signal and the health status indication signal from the indicator 130. The smart microphone and vocal analyzer thus enable the user to conveniently monitor the acoustic quality and health status whenever and wherever possible. Moreover, the user may continuously and objectively monitor the acoustic quality and health status, obviating the need to consult with a vocal trainer or a doctor.

Various appropriate forms of indication signals may be generated by the indicator 130. The signals may be an optical signal, an audio signal, a vibration signal, a text signal, a graphic signal, or a combination thereof. Optionally, the indicator 130 includes an indicator light for generating an optical signal. The optical signals may be of different colors or different intensities in response to different acoustic qualities and different health status. In one example, the indicator 130 includes a first indicator light of a first color and a second indicator light of a second color. When the signal transceiver 120 receives an acoustic quality determination signal, the indicator 130 generates a first indication signal to turn on the first indicator light. Different acoustic qualities correspond to different intensities of the light emitted from the first indicator light. When the signal transceiver 120 receives a health status determination signal, the indicator 130 generates a second indication signal to turn on the second indicator light. Different health status correspond to different intensities of the light emitted from the second indicator light. Optionally, the indicator 130 includes a display panel for generating an image signal as the indication signal. Optionally, the indicator 130 includes an audio play for generating an audio indication signal. Optionally, the indicator 130 includes a vibrator for generating a vibration indication signal.

Optionally, the voice status determination signal includes both the acoustic quality determination signal and the health status determination signal. Optionally, the vocal analyzer 200 is configured to determine both the acoustic quality and the health status of a user.

Referring to FIG. 1, the microphone 100 in some embodiments includes a biometric sensor 140 configured to detect one or more biometric signals of a user. The signal transceiver 120 is connected to the biometric sensor 140, and is configured to transmit the one or more biometric signals detected by the biometric sensor 140 to the vocal analyzer 200, which generates a health status determination signal based on the digital audio signal and the one or more biometric signals. The vocal analyzer 200 then transmits the health status determination signal to the microphone 100 (e.g., to the signal transceiver 120). Optionally, the one or more biometric signals includes one or a combination of a body temperature signal, a pulse wave signal, a blood oxygen level signal, a heart rate signal, and a blood pressure signal. Optionally, the biometric sensor 140 includes one or more of a temperature for detecting a body temperature, a pulse measuring device for detecting a pulse wave, an infrared sensor (e.g., a projection-type infrared sensor) for detecting a blood oxygen level and a heart rate, and a blood pressure measuring device for detecting a blood pressure.

Figure 2:
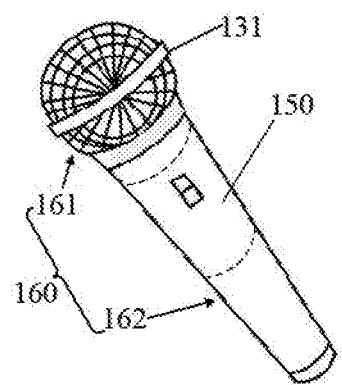
FIG. 2 is an exterior view of a microphone in some embodiments according to the present disclosure.

FIG. 2 is an exterior view of a microphone in some embodiments according to the present disclosure. Referring to FIG. 1 and FIG. 2, the microphone 100 in some embodiments includes a shell 160. The shell 160 in some embodiments includes a head part 161 and a handle part 162. Optionally, the voice sensor 110a is enclosed by the head part 161 of the shell 160. Optionally, the biometric sensor 140 is disposed on an outer wall of the handle part 162 of the shell 160, in order to have a compact and integrated structure. The indicator light of the indicator 130 can be enclosed by the head part 161 of the shell 160. The head part 161 is configured to allow light pass through. For example, the head part 161 may have a mesh structure. Optionally, the voice sensor 110a can also be enclosed by the mesh structure of the head part 161. Optionally, the indicator 130 includes a display panel 131, and the display panel 131 may be disposed on an outer wall of the shell 160. Optionally, the display panel 131 is disposed on an outer wall of the head part 161 of the shell 160, as depicted in FIG. 2. Optionally, the display panel 131 is disposed on an outer wall of the handle part 162 of the shell 160.

Referring to FIG. 1 and FIG. 2, the microphone 100 in some embodiments further includes an authenticator 150 configured to collect an identification information of a user. The signal transceiver 120 is connected to the authenticator 150 and configured to transmit the identification information, e.g., to the vocal analyzer 200. By having an authenticator 150, the vocal analyzer 200 can establish a personalized data base for each user based on the identification information of the user, the user's digital audio signal, and the acoustic quality and the health status of the user. The personalized data base facilitates tracking of the user's acoustic quality and health status.

In some embodiments, the authenticator 150 is disposed on the outer wall of the handle part 162 of the shell 160. Optionally, the identification information of the user includes a fingerprint information of the user. Optionally, the authenticator 150 includes a touch panel for collecting fingerprint of the user.

Figure 3:
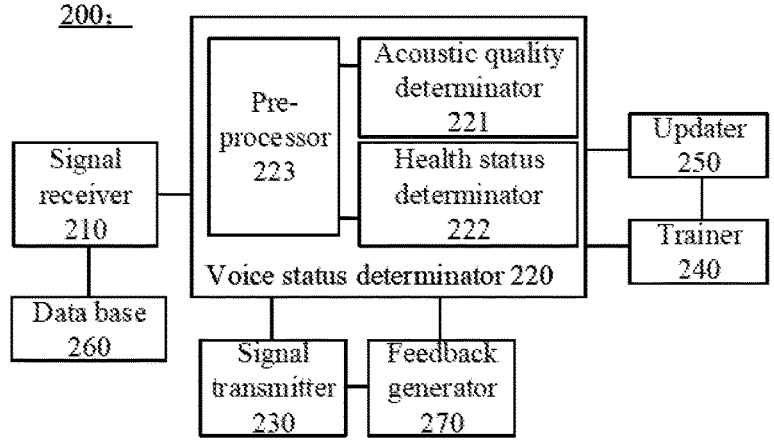
FIG. 3 is a schematic diagram illustrating the structure of a vocal analyzer in some embodiments according to the present disclosure.

In another aspect, the present disclosure provides a vocal analyzer. FIG. 3 is a schematic diagram illustrating the structure of a vocal analyzer in some embodiments according to the present disclosure. Referring to FIG. 3, the vocal analyzer 200 in some embodiments includes a signal receiver 210 configured to receive the digital audio signal transmitted by the signal transceiver 120; a voice status determinator 220 connected to the signal receiver 210 and configured to generate the voice status determination signal based, at least in part, on the digital audio signal; and a signal transmitter 230 connected to the voice status determinator 220 and configured to transmit the voice status determination signal to the signal transceiver 120. Optionally, the voice status determination signal includes an acoustic quality determination signal. Optionally, the voice status determination signal includes a health status determination signal.

In some embodiments, the voice status determination signal includes both an acoustic quality determination signal and a health status determination signal. Upon collecting an audio signal by the voice sensor 110a of the microphone 100, the audio signal is converted into a digital audio signal which is then transmitted to the vocal analyzer 200. The voice status determinator 220 of the vocal analyzer 200 is configured to determine an acoustic quality of the user based on the digital audio signal, thereby generating an acoustic quality determination signal. Optionally, the voice status determinator 220 of the vocal analyzer 200 is configured to determine a health status of the user based on the digital audio signal, thereby generating a health status determination signal. Subsequently, the signal transmitter 230 transmits the voice status determination signal (e.g., the acoustic quality determination signal or the health status determination signal) to the microphone 100. The indicator 130 of the microphone 100 generates one or more indication signals based on the voice status determination signal. Accordingly, the user may obtain an assessment on his or her acoustic quality or health status.

Optionally, the vocal analyzer 200 and the microphone 100 are integrated together. Optionally, one or more components of the vocal analyzer 200 (e.g., the voice status determinator 220, a pre-processor 223 of the voice status determinator 220, or a acoustic quality determinator 221 of the voice status determinator 220) are integrated into the microphone 100. In one example, the integrated apparatus is a smart microphone including a microphone 100 and the vocal analyzer 200 integrated into the microphone 100. Optionally, the vocal analyzer 200 and the microphone 100 are separate structures. Optionally, at least part of the vocal analyzer 200 may be in a cloud server in communication with the microphone 100.

Referring to FIG. 3, the voice status determinator 220 in some embodiments includes an acoustic quality determinator 221 configured to determine an acoustic quality of the digital audio signal. Optionally, the voice status determinator 220 further includes a health status determinator 222 configured to classify a health status of a user. Optionally, the voice status determinator 220 includes both an acoustic quality determinator 221 configured to determine an acoustic quality of the digital audio signal and a health status determinator 222 configured to classify a health status of a user.

In some embodiments, the acoustic quality determinator 221 is configured to determine the acoustic quality of the digital audio signal by calculating a degree of similarity between the digital audio signal and a target audio signal, e.g., a note in the digital audio signal and a target note. The degree of similarity is used as a representative of the acoustic quality. The higher the degree of similarity, the better the acoustic quality. As discussed above, the microphone 100 may be used for vocal training by a user, e.g., a singer or a news anchor. Optionally, the target audio signal may be a pre-collected audio signal. Optionally, the target audio signal may be an audio signal according to standard pronunciation. In one example, the target audio signal may include one or more pre-collected audio signals that span a vocal range and include a plurality of tones. When a user is engaged in a vocal training session, the user can try to reproduce the target audio signal. The microphone 100 coverts the user's sound into a digital audio signal, and transmits it to the vocal analyzer 200. The acoustic quality determinator 221 is configured to determine a degree of similarity between a sound produced by the user in the vocal training and the target audio signal, e.g., the degree of similarity in terms of a tune, a pitch, a volume of the sound.

In some embodiments, the degree of similarity between the digital audio signal and a target audio signal (e.g., between a note in the digital audio signal and a target note) is calculated using a first convolutional neural network model for enhanced efficiency and accuracy. Optionally, the first convolutional neural network model is a deep neural network model. Optionally, the first convolutional neural network model includes an input layer, a plurality of convolutional layers, a plurality of activation layers and fully connected layers. Optionally, the acoustic quality determinator 221 extracts one or more features from the digital audio signal, obtains one or more acoustic feature vectors of a certain length, and inputs the one or more acoustic feature vectors and acoustic feature vectors of a target audio signal into the input layer of the first convolutional neural network model. The first convolutional neural network model calculates the degree of similarity between the digital audio signal and the target audio signal, and output the degree of similarity from the fully connected layer. Optionally, the one or more features of the audio signal may be extracted by a Mel-scale Frequency Cepstral Coefficients (MFCC) extraction process.

The health status determinator 222 is configured to classify a health status of a user using one or more classification models. In some embodiments, the classification model is a second convolutional neural network model for enhanced classification efficiency and accuracy. Optionally, the second convolutional neural network model is a deep neural network model. Optionally, the second convolutional neural network model includes an input layer, a plurality of convolutional layers, a plurality of activation layers and fully connected layers. Optionally, the health status determinator 222 extracts one or more features from the digital audio signal, obtains one or more acoustic feature vectors of a certain length, and inputs the one or more acoustic feature vectors and acoustic feature vectors of a target audio signal into the input layer of the second convolutional neural network model. The second convolutional neural network model calculates a plurality of coefficients corresponding to a plurality of health status, and outputs the plurality of coefficients from the fully connected layer. Optionally, a health status among the plurality of health status having the largest coefficient among the plurality of coefficients represents a health status corresponding to the digital audio signal.

In some embodiments, the microphone 100 further includes a biometric sensor 140 configured to detect one or more biometric signals. Optionally, the signal receiver 210 is configured to receive the digital audio signal and the one or more biometric signals transmitted from the transceiver 120. Optionally, the health status determinator 222 is configured to classify a health status of a user based on a combination of the digital audio signal and the one or more biometric signals using one or more classification models, e.g., the second convolutional neural network model. Optionally, the health status determinator 222 extracts one or more features from the digital audio signal and one or more features from the one or more biometric signals, obtains one or more acoustic feature vectors and one or more biometric feature vectors, and inputs the one or more acoustic feature vectors, the one or more biometric feature vectors, and acoustic feature vectors of a target audio signal into the input layer of the second convolutional neural network model. The second convolutional neural network model calculates a plurality of coefficients corresponding to a plurality of health status, and outputs the plurality of coefficients from the fully connected layer. Optionally, a health status among the plurality of health status having the largest coefficient among the plurality of coefficients represents a health status corresponding to the digital audio signal.

Optionally, when the acoustic quality determinator 221 and the health status determinator 222 extracts one or more features from the digital audio signal, the extraction process is based on a wave information of the digital audio signal, e.g., the tune, the pitch, the volume of the sound, and not based on the linguistic information (e.g., specific words and sentences) of the digital audio signal.

In some embodiments, the voice status determinator 220 further includes a pre-processor 223 configured to pre-process the digital audio signal or the one or more biometric signals, thereby reducing or eliminating noises introduced during the collection and transmission of the digital audio signal or the one or more biometric signals. After the digital audio signal or the one or more biometric signals is processed by the pre-processor 223, the pre-processed digital audio signal is transmitted to the acoustic quality determinator 221, and the pre-processed one or more biometric signals are transmitted to the health status determinator 222. Optionally, the pre-processor 223 is configured to pre-process the digital audio signal or the one or more biometric signals using processes such as a filter-denoising process and a normalization process.

In some embodiments, the vocal analyzer further includes a trainer 240 for obtaining a similarity calculation model for calculating the degree of similarity or a classification model for classifying the health status. Optionally, the similarity calculation model is trained using a plurality of first reference audio signals and a plurality of reference degrees of similarity associate therewith. Optionally, the classification model is trained using a plurality of second reference audio signals, a plurality of reference biometric signals, and a plurality of reference health status classifications associated therewith.

In some embodiments, the similarity calculation model is the first convolutional neural network model. Optionally, the first convolutional neural network model is trained to obtain mapping relationships among nodes in various layers of the first convolutional neural network model. In one example, the training process includes first establishing a first sample data base. The first sample data base includes a plurality of pre-collected first reference audio signals and a plurality of reference degrees of similarity associated with the plurality of first reference audio signals (relative to a target audio signal). The training process further includes inputting the plurality of first reference audio signals and the target audio signal into the input layer of an initial first convolutional neural network model, and inputting the plurality of reference degrees of similarity into the fully connected layer of the initial first convolutional neural network model. The initial first convolutional neural network model is then trained multiple times to obtain the first convolutional neural network model.

In some embodiments, the classification model is the second convolutional neural network model. Optionally, the second convolutional neural network model is trained to obtain mapping relationships among nodes in various layers of the second convolutional neural network model. In one example, the training process includes first establishing a second sample data base. The second sample data base includes a plurality of reference health status types, e.g., "healthy vocal cord," "vocal cord fatigue," and "pathological change in vocal cord;" a plurality of pre-collected second reference audio signals; and a plurality of pre-collected biometric signals. The training process further includes inputting the plurality of pre-collected second reference audio signals and the plurality of pre-collected biometric signals into the input layer of an initial second convolutional neural network model, and inputting the plurality of reference health status types into the fully connected layer of the initial second convolutional neural network model. The nodes in the fully connected layer of the initial second convolutional neural network model corresponding to reference health status types corresponding to the plurality of pre-collected second reference audio signals and the plurality of pre-collected biometric signals are set to "1," and other nodes are set to "0." The initial second convolutional neural network model is then trained multiple times to obtain the second convolutional neural network model.

Optionally, the first convolutional neural network model and the second convolutional neural network model are trained using a Stochastic Gradient Descent method, e.g., a Moment-based Stochastic Gradient Descent method.

The input layer of the neural network model in the training process corresponds to the input layer of the neural network model in use. e.g., in the actual process of calculating the degree of similarity or the actual process of classifying the health status. As discussed above, the acoustic quality determinator 221 and the health status determinator 222 first extract one or more features from the digital audio signal, obtain one or more acoustic feature vectors, and subsequently input the one or more acoustic feature vectors into the input layer of the neural network model. Similarly, in the training process, extracted features of the reference audio signals are inputted into the input layer of the neural network model. Optionally, the plurality of first reference audio signals and the plurality of second reference audio signals used in the training process are also extracted features of the audio signals.

In some embodiments, the plurality of first reference audio signals and the plurality of second reference audio signals used in the training process are unextracted audio signals. The unextracted audio signals are inputted into the input layer of the neural network model. Accordingly, the digital audio signal from which the degree of similarity and the health status are to be determined is also an unextracted audio signal. Feature extraction is performed in the neural network model prior to the calculation of the degree of similarity and the classification of the health status.

Optionally, the health status of the user can also be classified based on the digital audio signal without the biometric signals. Accordingly, biometric signals are not needed in the training process of the second convolutional neural network model.

Referring to FIG. 3, the vocal analyzer 200 in some embodiments further includes an updater 250. The updater 250 is connected to the voice status determinator 220 and the trainer 240. The updater 250 is configured to update the similarity calculation model using a data including the digital audio signal and the degree of similarity calculated based on the digital audio signal; and update the classification model using a data including the digital audio signal, the one or more biometric signals, and the health status classified based on the digital audio signal and the one or more biometric signals. As discussed above, in the training process of the similarity calculation model, a first sample data base is first established; and in the training process of the classification model, a second sample data base is first established. The updating process in some embodiments includes updating the first sample data base with the data including the digital audio signal and the degree of similarity calculated based on the digital audio signal, thereby obtaining an updated first sample data base; and training the similarity calculation model using the updated first sample data base, thereby obtaining an updated similarity calculation model having enhanced accuracy. Optionally, the updating process includes updating the second sample data base with the data including the digital audio signal, the one or more biometric signals, and the health status classified based on the digital audio signal and the one or more biometric signals, thereby obtaining an updated second sample data base; and training the similarity calculation model using the updated second sample data base, thereby obtaining an updated classification model having enhanced accuracy.

In some embodiments, the microphone 100 further includes an authenticator 150 configured to collect an identification information of a user. Referring to FIG. 3, the vocal analyzer 200 in some embodiments further includes a data base 260 having a plurality of biometric information of a plurality of users, a plurality of acoustic quality information of the plurality of users, and optionally, a plurality of health status information of the plurality of users. The data base 260 enables a user to review his or her historical acoustic quality data and historical health status data.

Referring to FIG. 3, the vocal analyzer 200 in some embodiments further includes a feedback generator 270 connected to the voice status determinator 220. The feedback generator 270 is configured to generate a first feedback signal based on the acoustic quality of the digital audio signal and a second feedback signal based on the health status of the user. Optionally, the signal transmitter 230 is connected to the feedback generator 270, and is configured to transmit the first feedback signal or the second feedback signal to the microphone 100 (e.g., the signal transceiver 120 of the microphone 100). Optionally, the indicator 130 (e.g., a display panel of the indicator 130) is configured to display a plurality of vocal training instructions based on the first feedback signal and a plurality of health guidance instructions based on the second feedback signal.

In one example, the plurality of vocal training instructions are a plurality of pre-selected vocal training instructions. For example, the degree of similarity may be grouped into a plurality of ranges, each of which corresponding to one of the plurality of pre-selected vocal training instructions. When the voice status determinator 220 determines a degree of similarity for the digital audio signal, the signal transmitter 230 transmits one of the plurality of pre-selected vocal training instructions corresponding to one of the plurality of ranges containing the degree of similarity to the microphone 100. The microphone 100 receives the one of the plurality of pre-selected vocal training instructions. The display panel of the microphone 100 displays the one of the plurality of pre-selected vocal training instructions. Based on the one of the plurality of pre-selected vocal training instructions, a user can adjust his or her tune, pitch, and/or volume to match with the target audio signal, thereby perfecting his or her acoustic quality.

Similarly, the plurality of health guidance instructions may be a plurality of pre-selected health guidance instructions. For example, each of the plurality of pre-selected health guidance instructions may corresponds to one of a plurality of health status. When the voice status determinator 220 classifies a health status of the user, the signal transmitter 230 transmits one of the plurality of pre-selected health guidance instructions corresponding to the health status to e microphone 100. The microphone 100 receives the one of the plurality of pre-selected health guidance instructions. The display panel of the microphone 100 displays the one of the plurality of pre-selected health guidance instructions. Based on the one of the plurality of pre-selected health guidance instructions, a user can adjust his or her practice intensity. For example, when the health status is "vocal cord fatigue," the one of the plurality of pre-selected health guidance instructions may be "take a break."

Figure 4:
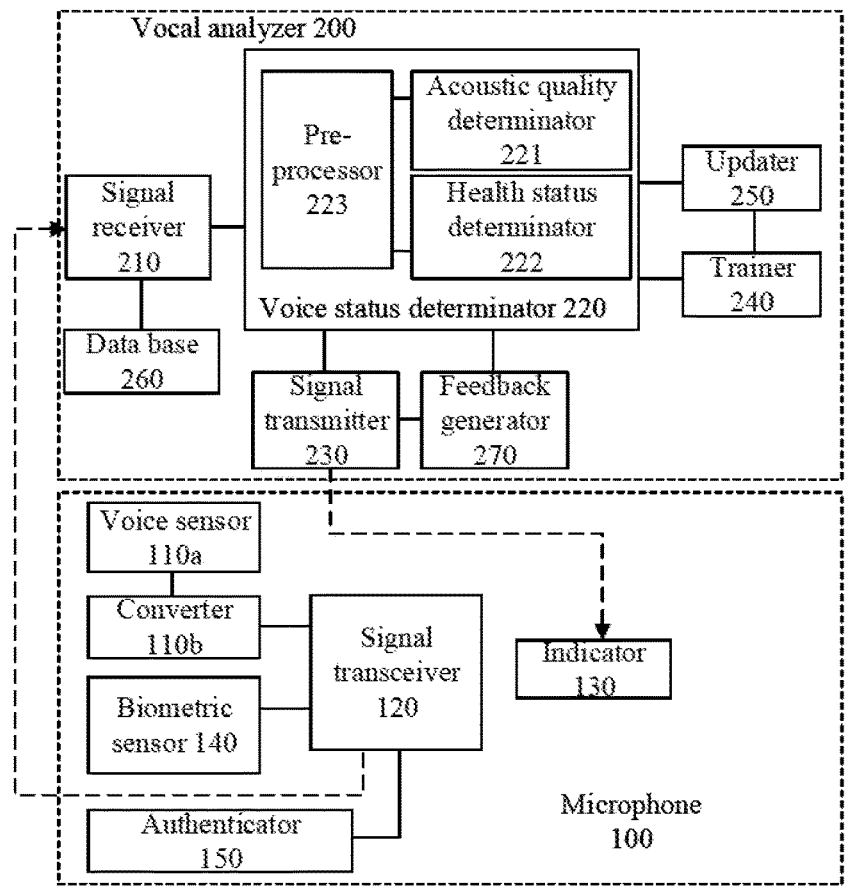
FIG. 4 is a schematic diagram illustrating the structure of a vocal training apparatus in some embodiments according to the present disclosure.

In another aspect, the present disclosure provides a vocal training apparatus. FIG. 4 is a schematic diagram illustrating the structure of a vocal training apparatus in some embodiments according to the present disclosure. Referring to FIG. 4, the vocal training apparatus in some embodiments includes the microphone 100 and the vocal analyzer 200. The signal transceiver 120 of the microphone 100 is in communication with the signal receiver 210 of the vocal analyzer 200. The indicator 130 of the microphone 100 is in communication with the signal transmitter 230 of the vocal analyzer 200. In one example, the microphone 100 collects an audio signal of a user, the vocal analyzer 200 generates a vocal status determination signal, and the indicator 130 of the microphone 100 displays an indication signal. Optionally, the vocal training apparatus is a smart microphone having the microphone 100 and the vocal analyzer 200 integrated into the microphone 100. For example, the vocal analyzer 200 may be integrated into the shell of the microphone 100. Optionally, the vocal analyzer 200 and the microphone 100 are separate structures. Optionally, at least part of the vocal analyzer 200 may be in a cloud server in communication with the microphone 100.

In some embodiments, the vocal training apparatus may be integrated into a smart device such as a smart phone, a smart watch, a MP3 player, a game console, a headphone, a computer, a tablet, a laptop, and a home theater system.

The present vocal training apparatus enables a user to conveniently monitor the acoustic quality and health status whenever and wherever possible. Accordingly, the user may continuously and objectively monitor the acoustic quality and health status.

Figure 5:
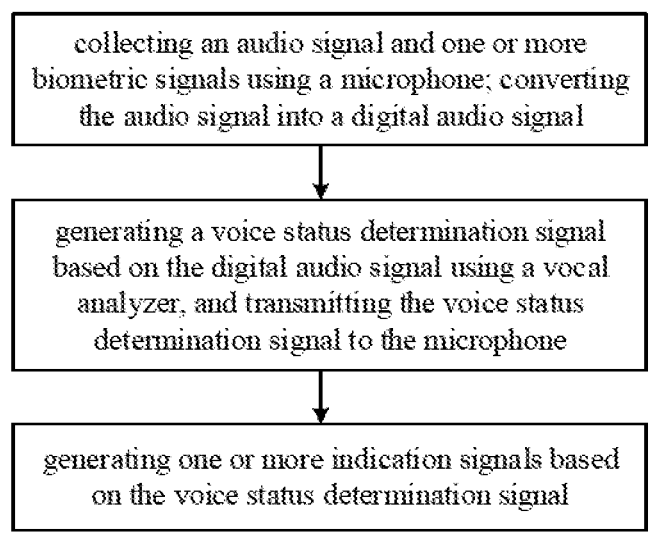
FIG. 5 is a flow chart illustrating a vocal training method in some embodiments according to the present disclosure.

In another aspect, the present disclosure provides a vocal training method. FIG. 5 is a flow chart illustrating a vocal training method in some embodiments according to the present disclosure. Referring to FIG. 5, the method in some embodiments includes collecting an audio signal and one or more biometric signals using a microphone; converting the audio signal into a digital audio signal; generating a voice status determination signal based on the digital audio signal using a vocal analyzer, transmitting the voice status determination signal to the microphone; and generating one or more indication signals based on the voice status determination signal. Optionally, the step of generating the voice status determination signal includes generating an acoustic quality determination signal based on the digital audio signal.

In some embodiments, the voice status determination signal includes an acoustic quality determination signal. Optionally, the voice status determination signal includes a health status determination signal. Optionally, the voice status determination signal includes both an acoustic quality determination signal and a health status determination signal. In some embodiments, the one or more indication signals include an acoustic quality indication signal. Optionally, the one or more indication signals include a health status indication signal. Optionally, the one or more indication signals include both an acoustic quality indication signal and a health status indication signal.

Optionally, the method further includes detecting one or more biometric signals of the user (e.g., by the microphone); generating a health status determination signal based on a combination of the digital audio signal and the one or more biometric signals (e.g., by the vocal analyzer); transmitting the health status determination signal to the microphone; and generating a health status indication signal based on the health status determination signal.

In some embodiments, the step of determining the acoustic quality of the digital audio signal includes calculating a degree of similarity between the digital audio signal and a target audio signal, e.g., calculating a degree of similarity between a note in the digital audio signal and a target note. Optionally, the step of calculating the degree of similarity is performed using a first convolutional neural network model. Optionally, the step of calculating the degree of similarity is performed using a similarity calculation model trained using a plurality of first reference audio signals and a plurality of reference degrees of similarity associate therewith. Optionally, the method further includes training a similarity calculation model using a plurality of first reference audio signals and a plurality of reference degrees of similarity associate therewith. Optionally, the method further includes updating the similarity calculation model using a data comprising the digital audio signal and the degree of similarity calculated based on the digital audio signal.

In some embodiments, the step of generating the health status determination signal includes classifying a health status of a user based on the digital audio signal and the one or more biometric signals. Optionally, the step of classifying the health status of a user is performed using a second convolutional neural network model. Optionally, the step of classifying the health status of a user is performed using a classification model trained using a plurality of second reference audio signals, a plurality of reference biometric signals, and a plurality of reference health status classifications associated therewith. Optionally, the method further includes training a classification model using a plurality of second reference audio signals, a plurality of reference biometric signals, and a plurality of reference health status classifications associated therewith. Optionally, the method further includes updating the classification model using a data comprising the digital audio signal, the one or more biometric signals, and the health status classified based on the digital audio signal and the one or more biometric signals.

In some embodiments, the method further includes pre-processing the digital audio signal. Optionally, the method further includes pre-processing the one or more biometric signals. Optionally, the pre-processing is performed by a filter-denoising process or a normalization process or a combination thereof.

In some embodiments, the method further includes collecting an identification information of a user in order to authenticate the user. Optionally, the vocal analyzer further includes a data base having a plurality of biometric information of a plurality of users. Optionally, the data base further includes a plurality of acoustic quality information of the plurality of users and a plurality of health status information of the plurality of users. Optionally, the method further includes storing the biometric information of the user in the data base. Optionally, the method further includes storing the plurality of acoustic quality information of the user and the plurality of health status information of the user in the data base.

In some embodiments, the method further includes generating a first feedback signal based on the acoustic quality of the digital audio signal. Optionally, the step of generating one or more indication signals includes generating the one or more indication signals based on the first feedback signal. Optionally, the method further includes generating a second feedback signal based on the health status of the user. Optionally, the step of generating one or more indication signals includes generating the one or more indication signals based on the second feedback signal.

Figure 6:
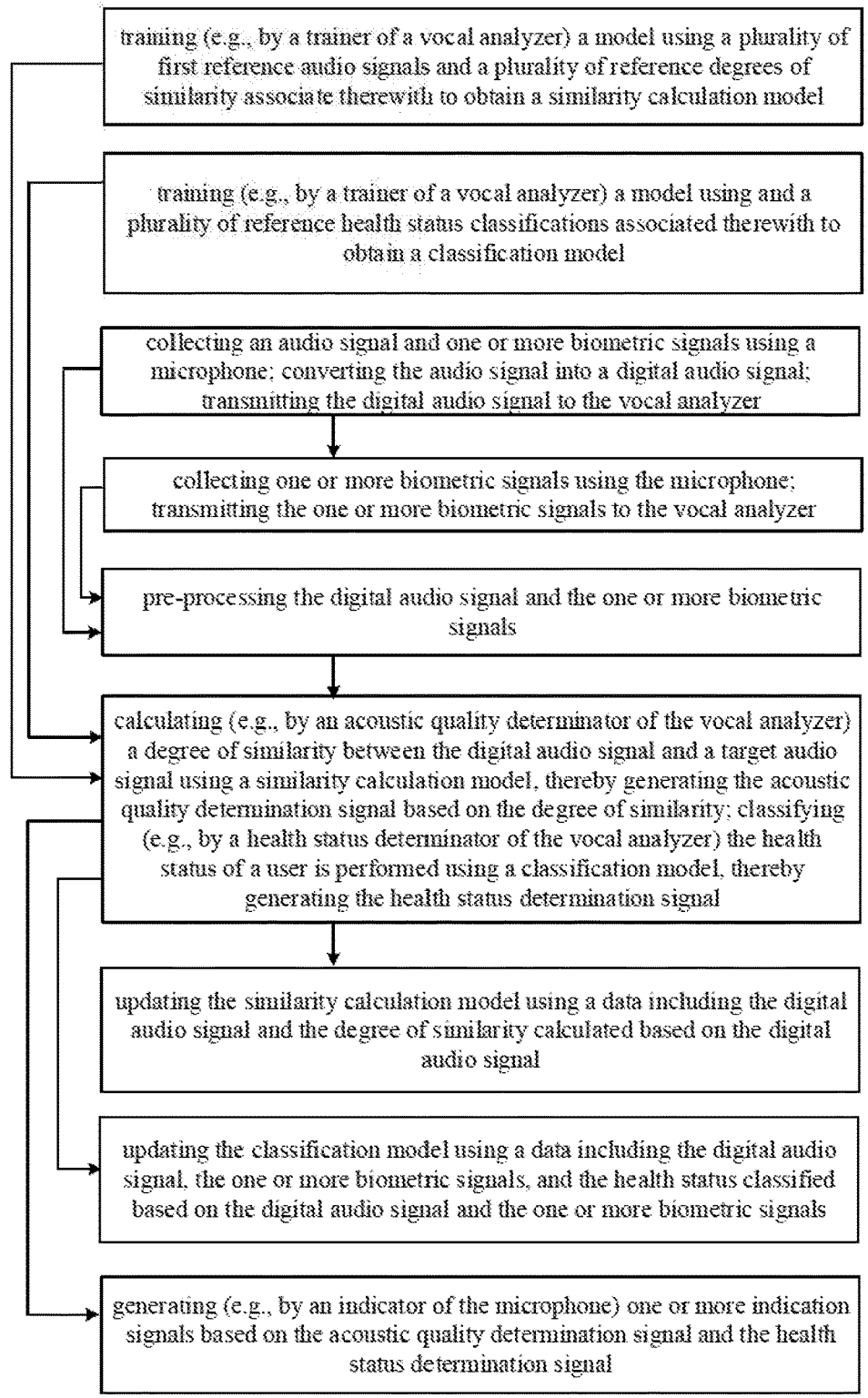
FIG. 6 is a flow chart illustrating a vocal training method in some embodiments according to the present disclosure.

FIG. 6 is a flow chart illustrating a vocal training method in some embodiments according to the present disclosure. Referring to FIG. 6, the method in some embodiments includes training (e.g., by a trainer of a vocal analyzer) a model using a plurality of first reference audio signals and a plurality of reference degrees of similarity associate therewith to obtain a similarity calculation model (e.g., a first convolutional neural network model); using a plurality of second reference audio signals, a plurality of reference biometric signals, training (e.g., by a trainer of a vocal analyzer) a model using and a plurality of reference health status classifications associated therewith to obtain a classification model (e.g., a second convolutional neural network model); collecting an audio signal and one or more biometric signals using a microphone; converting the audio signal into a digital audio signal; transmitting the digital audio signal to the vocal analyzer, collecting one or more biometric signals using the microphone; and transmitting the one or more biometric signals to the vocal analyzer.

In some embodiments, the method further includes generating (e.g., by the vocal analyzer) a voice status determination signal and transmitting the voice status determination signal to the microphone. Referring to FIG. 6, in some embodiments, the step of generating the voice status determination signal includes pre-processing the digital audio signal and the one or more biometric signals; calculating (e.g., by an acoustic quality determinator of the vocal analyzer) a degree of similarity between the digital audio signal and a target audio signal using a similarity calculation model, thereby generating the acoustic quality determination signal based on the degree of similarity; classifying (e.g., by a health status determinator of the vocal analyzer) the health status of a user is performed using a classification model, thereby generating the health status determination signal. Optionally, the degree of similarity is calculated using a digital audio signal that has been pre-processed, e.g., the degree of similarity between a pre-processed digital audio signal and the target audio signal. Optionally, the health status is classified using a digital audio signal and the one or more biometric signals that have been pre-processed, e.g., the health status classified based on a pre-processed digital audio signal and pre-processed one or more biometric signals.

In some embodiments, and referring to FIG. 6, the method further includes updating the similarity calculation model using a data including the digital audio signal and the degree of similarity calculated based on the digital audio signal. Optionally, the method further includes updating the classification model using a data including the digital audio signal, the one or more biometric signals, and the health status classified based on the digital audio signal and the one or more biometric signals.

In some embodiments, and referring to FIG. 6, the method further includes generating (e.g., by an indicator of the microphone) one or more indication signals based on the acoustic quality determination signal and the health status determination signal.

The present vocal training method enables a user to conveniently monitor the acoustic quality and health status whenever and wherever possible. Accordingly, the user may continuously and objectively monitor the acoustic quality and health status, obviating the need to consult with a vocal trainer or a doctor. By using a combination of the digital audio signal and the one or more biometric signals in determining the health status of a user, the health status can be determined more accurately. Further, the user may review his or her historical acoustic quality data and historical health status data.

In another aspect, the present disclosure provides a non-transitory tangible computer-readable storage medium storing computer-readable instructions. In some embodiments, the computer-readable instructions being executable by a processor to cause the processor to perform generating a voice status determination signal based on the digital audio signal using a vocal analyzer; and generating one or more indication signals based on the voice status determination signal. Optionally, generating the voice status determination signal includes generating an acoustic quality determination signal based on the digital audio signal. Optionally, generating the voice status determination signal includes generating a health status determination signal, e.g., based on a combination of the digital audio signal and the one or more biometric signals. Optionally, generating the one or more indication signals includes generating an acoustic quality indication signal based on the acoustic status determination signal. Optionally, generating the one or more indication signals includes generating a health status indication signal based on the health status determination signal.

In some embodiments, the computer-readable instructions being executable by a processor to cause the processor to perform calculating a degree of similarity between the digital audio signal and a target audio signal, e.g., calculating a degree of similarity between a note in the digital audio signal and a target note. Optionally, calculating the degree of similarity is performed using a first convolutional neural network model. Optionally, calculating the degree of similarity is performed using a similarity calculation model trained using a plurality of first reference audio signals and a plurality of reference degrees of similarity associate therewith. Optionally, the computer-readable instructions being executable by a processor to cause the processor to perform updating the similarity calculation model using a data comprising the digital audio signal and the degree of similarity calculated based on the digital audio signal.

In some embodiments, the computer-readable instructions being executable by a processor to cause the processor to perform classifying a health status of a user based on the digital audio signal and the one or more biometric signals. Optionally, classifying the health status of a user is performed using a second convolutional neural network model. Optionally, classifying the health status of a user is performed using a classification model trained using a plurality of second reference audio signals, a plurality of reference biometric signals, and a plurality of reference health status classifications associated therewith. Optionally, the computer-readable instructions being executable by a processor to cause the processor to perform updating the classification model using a data comprising the digital audio signal, the one or more biometric signals, and the health status classified based on the digital audio signal and the one or more biometric signals.

In some embodiments, the computer-readable instructions being executable by a processor to cause the processor to perform pre-processing the digital audio signal. Optionally, the computer-readable instructions being executable by a processor to cause the processor to perform pre-processing the one or more biometric signals. Optionally, the pre-processing is performed by a filter-denoising process or a normalization process or a combination thereof.

In some embodiments, the computer-readable instructions being executable by a processor to cause the processor to perform generating a first feedback signal based on the acoustic quality of the digital audio signal. Optionally, the computer-readable instructions being executable by a processor to cause the processor to perform generating the one or more indication signals based on the first feedback signal. Optionally, the computer-readable instructions being executable by a processor to cause the processor to perform generating a second feedback signal based on the health status of the user. Optionally, the computer-readable instructions being executable by a processor to cause the processor to perform generating the one or more indication signals based on the second feedback signal.

The foregoing description of the embodiments of the invention has been presented for purposes of illustration and description. It is not intended to be exhaustive or to limit the invention to the precise form or to exemplary embodiments disclosed. Accordingly, the foregoing description should be regarded as illustrative rather than restrictive. Obviously, many modifications and variations will be apparent to practitioners skilled in this art. The embodiments are chosen and described in order to explain the principles of the invention and its best mode practical application, thereby to enable persons skilled in the art to understand the invention for various embodiments and with various modifications as are suited to the particular use or implementation contemplated. It is intended that the scope of the invention be defined by the claims appended hereto and their equivalents in which all terms are meant in their broadest reasonable sense unless otherwise indicated. Therefore, the term "the invention", "the present invention" or the like does not necessarily limit the claim scope to a specific embodiment, and the reference to exemplary embodiments of the invention does not imply a limitation on the invention, and no such limitation is to be inferred. The invention is limited only by the spirit and scope of the appended claims. Moreover, these claims may refer to use "first", "second", etc. following with noun or element. Such terms should be understood as a nomenclature and should not be construed as giving the limitation on the number of the elements modified by such nomenclature unless specific number has been given. Any advantages and benefits described may not apply to all embodiments of the invention. It should be appreciated that variations may be made in the embodiments described by persons skilled in the art without departing from the scope of the present invention as defined by the following claims. Moreover, no element and component in the present disclosure is intended to be dedicated to the public regardless of whether the element or component is explicitly recited in the following claims.

What is claimed is:

1. A vocal training apparatus, comprising a microphone and a vocal analyzer;
   wherein the vocal analyzer comprises:
   a signal receiver configured to receive a digital audio signal and one or more biometric signals from the microphone;
   a voice status determinator connected to the signal receiver and configured to generate a voice status determination signal based on the digital audio signal, wherein the voice status determination signal comprises one or a combination of an acoustic quality determination signal and a health status determination signal; and
   a signal transmitter connected to the voice status determinator and configured to transmit the voice status determination signal to the microphone;
   the voice status determinator further comprises a health status determinator configured to:
   extract one or more features from the digital audio signal and generate one or more acoustic feature vectors based on the one or more features from the digital audio signal;
   extract one or more features from the one or more biometric signals and generate one or more biometric feature vectors based on the one or more features from the one or more biometric signals;
   input the one or more acoustic feature vectors and the one or more biometric feature vectors into an input layer of a convolutional neural network;
   calculate a plurality of coefficients respectively corresponding to a plurality of health status based on the one or more acoustic feature vectors and the one or more biometric feature vectors;
   assign one of the plurality of health status corresponding to a largest coefficient among the plurality of coefficients as the health status of the user; and
   generate the health status determination signal based on the health status assigned by the convolutional neural network.

2. The vocal training apparatus of claim 1, wherein the microphone comprises:
   a voice sensor configured to collect an audio signal;
   a converter connected to the voice sensor and configured to convert the audio signal into the digital audio signal;
   a signal transceiver connected to the converter and configured to transmit the digital audio signal to the signal receiver and receive the voice status determination signal from the signal transmitter; and
   an indicator configured to generate one or more indication signals based on the voice status determination signal;
   wherein the voice status determination signal comprises one or a combination of an acoustic quality determination signal and the health status determination signal; and
   the one or more indication signals comprises one or a combination of an acoustic quality indication signal and a health status indication signal.

3. The vocal training apparatus of claim 2, further comprising a biometric sensor configured to detect the one or more biometric signals;
   wherein the health status determination signal is generated based on a combination of the digital audio signal and the one or more biometric signals;
   the signal transceiver is connected to the biometric sensor, and configured to transmit the one or more biometric signals detected by the biometric sensor to the signal receiver and receive the health status determination signal from the signal transmitter; and
   the one or more indication signals comprises the health status indication signal.

4. The vocal training apparatus of claim 3, wherein the one or more biometric signals comprises one or a combination of a body temperature signal, a pulse wave signal, a blood oxygen level signal, a heart rate signal, and a blood pressure signal.

5. The vocal training apparatus of claim 3, wherein the indicator comprises one or a combination of:
   an indicator light for generating an optical signal; and
   a display panel for generating an image signal.

6. The vocal training apparatus of claim 5, wherein the microphone comprises a shell;
   the shell comprises a head part and a handle part;
   the voice sensor is enclosed by the head part of the shell;
   the biometric sensor is on an outer wall of the handle part of the shell;
   the indicator light is enclosed by the head part of the shell which is configured to allow light pass through; and
   the display panel is on the outer wall of the handle part.

7. The vocal training apparatus of claim 6, further comprising an authenticator configured to collect an identification information of a user;
   the signal transceiver is connected to the authenticator and configured to transmit the identification information.

8. The vocal training apparatus of claim 7, wherein the authenticator is on the outer wall of the handle part; and
   the identification information of the user includes a fingerprint information of the user.

9. The vocal training apparatus of claim 2, wherein the microphone further comprises a biometric sensor configured to detect the one or more biometric signals; and
   the signal transceiver is connected to the biometric sensor, and configured to transmit the one or more biometric signals detected by the biometric sensor to the signal receiver and receive the health status determination signal from the signal transmitter.

10. The vocal training apparatus of claim 9, wherein the voice status determinator further comprises a pre-processor configured to pre-process the digital audio signal and the one or more biometric signals.

11. The vocal training apparatus of claim 9, wherein the vocal analyzer further comprises a feedback generator connected to the voice status determinator and configured to generate a first feedback signal based on the acoustic quality of the digital audio signal and a second feedback signal based on the health status of the user;

the signal transmitter is connected to the feedback generator and configured to transmit the first feedback signal and the second feedback signal to the signal transceiver; and the indicator comprises a display panel configured to display a plurality of vocal training instructions based on the first feedback signal and a plurality of health guidance instructions based on the second feedback signal.

12. The vocal training apparatus of claim 1, wherein the voice status determinator comprises an acoustic quality determinator configured to determine an acoustic quality of the digital audio signal by calculating a degree of similarity between a note in the digital audio signal and a target note.

13. The vocal training apparatus of claim 12, wherein the degree of similarity between a note in the digital audio signal and a target note is calculated using a first convolutional neural network model.

14. The vocal training apparatus of claim 12, wherein the degree of similarity between a note in the digital audio signal and a target note is calculated based a similarity calculation model trained using a plurality of first reference audio signals and a plurality of reference degrees of similarity associate therewith; and the health status of the user is classified based on a classification model trained using a plurality of second reference audio signals, a plurality of reference biometric signals, and a plurality of reference health status classifications associated therewith.

15. The vocal training apparatus of claim 14, further comprising an updater connected to the voice status determinator and configured to:

update the similarity calculation model using a data comprising the digital audio signal and the degree of similarity calculated based on the digital audio signal; and update the classification model using a data comprising the digital audio signal, the one or more biometric signals, and the health status classified based on the digital audio signal and the one or more biometric signals.

16. The vocal training apparatus of claim 2 wherein the microphone further comprises an authenticator configured to collect an identification information of a user;

the signal transceiver is connected to the authenticator and configured to transmit the identification information to the signal receiver;

the vocal analyzer further comprises a data base comprising a plurality of biometric information of a plurality of users, a plurality of acoustic quality information of the plurality of users, and a plurality of health status information of the plurality of users.

17. A vocal training method, comprising:
collecting an audio signal;
converting the audio signal into a digital audio signal;
detecting one or more biometric signals from a user;
extracting one or more features from the digital audio signal and generate one or more acoustic feature vectors based on the one or more features from the digital audio signal;
extracting one or more features from the one or more biometric signals and generate one or more biometric feature vectors based on the one or more features from the one or more biometric signals;
inputting the one or more acoustic feature vectors and the one or more biometric feature vectors into an input layer of a convolutional neural network;
calculating a plurality of coefficients respectively corresponding to a plurality of health status based on the one or more acoustic feature vectors and the one or more biometric feature vectors;
assigning one of the plurality of health status corresponding to a largest coefficient among the plurality of coefficients as the health status of the user;
generating the health status determination signal based on the health status assigned by the convolutional neural network; and
generating a voice status determination signal based on the digital audio signal, wherein the voice status determination signal comprises combination of an acoustic quality determination signal and the health status determination signal.

18. A non-transitory tangible computer-readable storage medium storing computer-readable instructions, the computer-readable instructions being executable by a processor to cause the processor to perform:
obtaining a digital audio signal;
obtaining one or more biometric signals;
extracting one or more features from the digital audio signal and generate one or more acoustic feature vectors based on the one or more features from the digital audio signal;
extracting one or more features from the one or more biometric signals and generate one or more biometric feature vectors based on the one or more features from the one or more biometric signals;
inputting the one or more acoustic feature vectors and the one or more biometric feature vectors into an input layer of a convolutional neural network;
calculating a plurality of coefficients respectively corresponding to a plurality of health status based on the one or more acoustic feature vectors and the one or more biometric feature vectors;
assigning one of the plurality of health status corresponding to a largest coefficient among the plurality of coefficients as the health status of the user;
generating the health status determination signal based on the health status assigned by the convolutional neural network; and
generating a voice status determination signal based on the digital audio signal, wherein the voice status determination signal comprises combination of an acoustic quality determination signal and the health status determination signal.

* * * * *